United States Patent

Sakurada et al.

Patent Number: 5,993,843
Date of Patent: Nov. 30, 1999

[54] BIODEGRADABLE SUSTAINED-RELEASE PREPARATION

[75] Inventors: Toyohisa Sakurada; Hiroshi Suzuki, both of Niigata-ken, Japan

[73] Assignee: Research Association for Biotechnology of Agricultural, Tokyo, Japan

[21] Appl. No.: 08/883,746

[22] Filed: Jun. 27, 1997

[30] Foreign Application Priority Data

Jun. 28, 1996 [JP] Japan .................................. 8-168898
Jun. 28, 1996 [JP] Japan .................................. 8-168899
Jun. 28, 1996 [JP] Japan .................................. 8-168900

[51] Int. Cl.$^6$ ............................ A01N 25/08; A01N 25/34
[52] U.S. Cl. ........................... 424/409; 424/403; 424/405; 424/407
[58] Field of Search .................................. 424/403, 405, 424/407, 409; 514/772.3

[56] References Cited

FOREIGN PATENT DOCUMENTS 5-163110   6/1993   Japan .
6-116103   4/1994   Japan .

Primary Examiner—Carlos A. Azpuru
Attorney, Agent, or Firm—McAulay Nissen Goldberg Kiel & Hand, LLP

[57] ABSTRACT

Described are a biodegradable sustained-release preparation which comprises a mixture of 99 to 10 parts by weight of an aliphatic polyester and 1 to 90 parts by weight of a modifier for the regulation of sustained releasability of an active ingredient, and the active ingredient held by said mixture; a biodegradable pheromone dispenser, wherein an aliphatic polyester is used as a sustained release layer for a pheromone contained therein as a liquid phase, said aliphatic polyester having recurring units whose ratio (I/II) of (I) the number of the carbon atoms constituting the main chain and not relating to ester linkage to (II) the number of the carbon atoms constituting the ester linkage is 2 or larger; and a biodegradable pest controlling agent which is obtained by mixing and dispersing an active ingredient and a carrier for holding said active ingredient in a biodegradable aliphatic polyester or which comprises 2 to 60 wt. % of an active ingredient, 30 to 95 wt. % of a biodegradable aliphatic polyester and 2 to 50 wt. % of a carrier for holding the active ingredient.

9 Claims, 5 Drawing Sheets

FIG.2
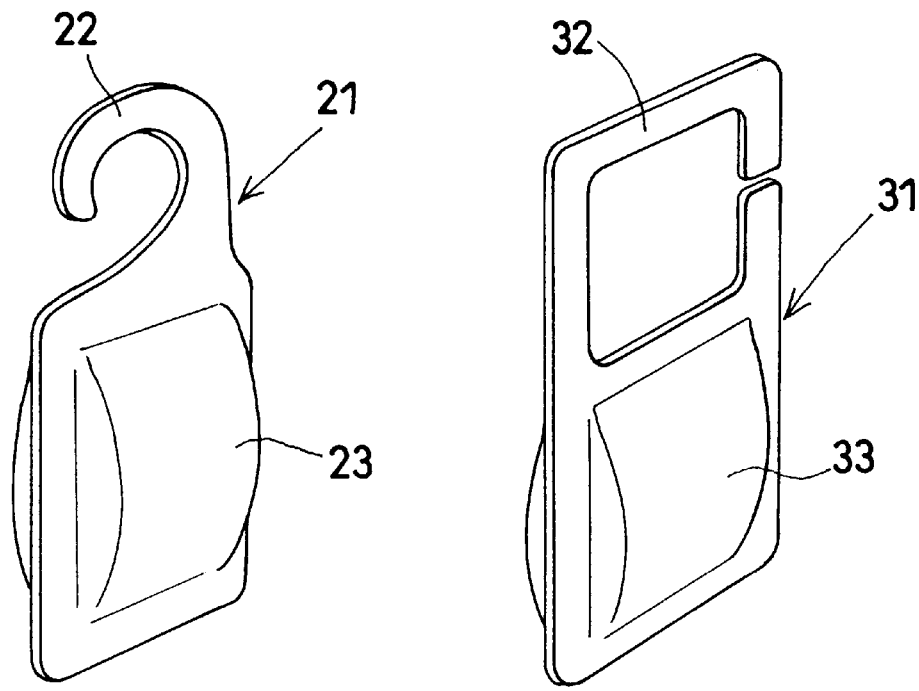
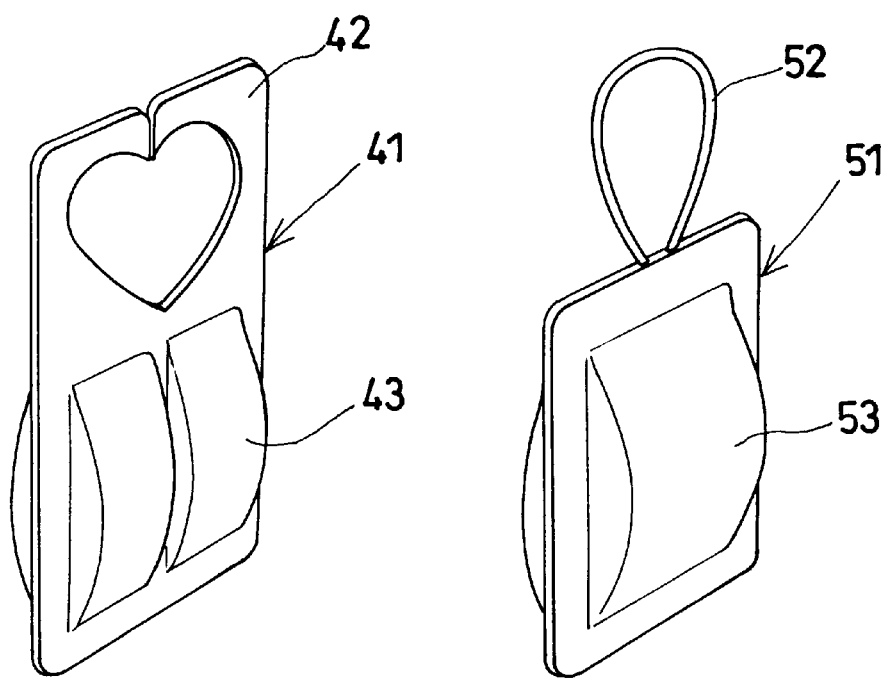

BIODEGRADABLE SUSTAINED-RELEASE PREPARATION

BACKGROUND OF THE INVENTION

A first group of this invention relates to a biodegradable sustained-release preparation.

In recent years, sustained release of an active ingredient has attracted attentions in various fields. For example, there are an aromatic which imparts refreshing taste to the air in a room and as a pest controlling means, a mating disruption agent making use of a sex pheromone and an attracting insecticide in which the mating disruption agent and insecticide are used in combination.

These agents are required to have durable effects for a long period of time so that an excellent technique for sustained release is necessary. Recently, they are desired to have biodegradability in addition.

For example, a mating disruption agent, attracting insecticide or the like used for agricultural purposes is hardly collected after use and most of them are left alone in the upland field or the like. Because, collection of such an agent, which has been distributed in a large amount, after application requires many hands and is therefore substantially impossible. The aromatic used indoors is disposed as rubbish. Since plastic waste matters generate much heat at the time of incineration, thereby damaging an incinerator, they are often buried in the ground. Accordingly, there is a demand for a biodegradable type sustained-release preparation which can be degraded by microorganisms at the time when buried in the ground and does not remain in the soil.

In recent years, various materials having biodegradability have been proposed and some of them have already been industrialized. They can be classified into some groups from the viewpoint of the raw material constituting them. Examples include cellulose type, starch-added type, aliphatic polyester type and polyvinyl alcohol type. They are used suitably in consideration of their characteristics such as applications or price, however, an aliphatic polyester type is preferred for the sustained release of an active ingredient.

For the agricultural applications where an agent tends to be left alone in the field after application, described in Japanese Patent Application Laid-Open No. 6-116103 is a pest controlling agent comprising a biodegradable aliphatic polyester and an active ingredient. The present inventor has already developed, as a sustained-release pheromone preparation having biodegradability, a sustained-release pheromone preparation comprising as a sustained-release layer, a polymer composed mainly of 3-hydroxybutyric acid (Japanese Patent Application Laid-Open No. 5-163110).

As described above, an aliphatic polyester type preparation is used preferably as a sustained-release preparation having biodegradability. In the aliphatic polyester, however, molecular chains are firmly bonded statically through an ester linkage in its structure, which makes it difficult for the active ingredient to diffuse the gap of the polymer segment, resulting in small transmittance of the active ingredient through the aliphatic polyester. The aliphatic polyester is therefore accompanied with the problem that a release surface area should be widened in order to increase the transpiration amount of the active ingredient or a number of sustained release preparations should be placed in order to secure a certain concentration.

A second group of the present invention relates to a biodegradable pheromone dispenser.

In recent years, as a pest controlling means, a controlling method making use of a pheromone has attracted attentions because it is safe and besides, it does not impart the pest insects with resistance.

A pheromone dispenser is requested to release a pheromone stably for a long period of time in order to deal with the breeding of pest insects over a breeding season and is also requested to have applicability to crops or other things to be treated. Various pheromone dispensers equipped with both excellent release performance and easy applicability have therefore been proposed.

The pheromone dispensers so far proposed can be classified into three types based on their shapes. The first one is a microcapsule or hollow fiber type used for distribution. The second one is a matrix type wherein a pheromone has been dispersed in a polymeric material. The third one is a so-called reservoir type in which a pheromone has been held as a liquid. The microcapsule or hollow fiber type can be applied easily by distribution or the like but involves a problem such as short control period. The matrix type is accompanied with the problem that the release rate of a pheromone depends on the pheromone concentration in the polymeric material so that the release rate inevitably shows a gradual decrease. Accordingly, as a pheromone dispenser, the reservoir type whose intra-membrane concentration gradient does not change so much has been rated high because of stable release performance over a long period of time.

It is however the present situation that most of such pheromone dispensers are not collected after application to the field such as upland field and are left alone in the field.

There has accordingly been a demand for a biodegradable type pheromone dispenser which is degraded in the soil and does not remain in the field and various proposals have already been made.

For example, in Japanese Patent Application Laid-Open No. 6-116103, a pest controlling agent made of a biodegradable aliphatic polyester is described. Described are a spherical pest controlling agent wherein the surface of an active ingredient in the form of a microcapsule has been covered with a biodegradable polymeric material; a spherical-, film- or ribbon-shaped material obtained by dispersing an active ingredient in a biodegradable polymeric material and then forming or molding the resulting dispersion; a film-shaped material having a barrier layer on its surface; and an adhesive-layer-having agent permitting easy application. Also described in it is a method of encapsulating an active ingredient in a capillary-shaped tube and releasing an active ingredient from the opening portion of the capillary tube. It is however difficult to secure stable release over a long period of time by such pest controlling agents.

As describe above, the present inventor has already proposed (Japanese Patent Application Laid-Open No. 5-163110) a sustained-release pheromone preparation using, as a sustained-release layer, a polymer composed mainly of 3-hydroxybutyric acid. Use of this polymer however requires a decrease in the thickness of the sustained-release layer or an increase in the release surface area, because this polymer has a small transmittance rate of a pheromone.

As such, a polyester is a substance having a small transmittance of pheromones and is not suited for use as a material for a reservoir type pheromone dispenser. Described specifically, aromatic polyesters such as polyethylene terephthalate hardly transmits pheromones. Aliphatic polyesters are not always same in the transmittance of pheromones. Under such situations, the kind and thickness of the aliphatic polyester appropriate for a sustained-release layer of a reservoir type pheromone dispenser having both biodegradability and sustained release property of pheromones have not yet been made cleared.

A third group of the present invention relates to a biodegradable pest controlling agent.

There are various methods to control harmful microorganisms which cause damage to field crops or horticultural crops. As described above, mating disruption agents and attracting insecticides making use of the sex pheromone of an insect have recently drawn attentions as excellent controlling means from the environmental viewpoint.

A variety of such controlling agents have been proposed and some of them have already been industrialized. Examples include, as described above, a polyethylene-made capillary tube or container made of an ethylene-vinyl acetate copolymer encapsulating an active ingredient; a polyvinyl chloride sheet having an active ingredient kneaded therein; a hollow fiber having an active ingredient enclosed therein; and a polyvinyl chloride sheet, which has an active ingredient kneaded therein, cut into small pieces to permit aerial application. It is the present situation that most of such agents are not collected after application and are left alone in the field.

There is accordingly a demand for a biodegradable pest controlling agent which is degraded in the soil and does not remain in the field.

As described above, the present inventor has proposed a biodegradable sustained-control pheromone preparation using, as a sustained-release layer, a polymer mainly composed of 3-hydroxybutyric acid in Japanese Patent Application Laid-Open No. 5-163110. Use of this polymer however requires a decrease in the thickness of the sustained-release layer or an increase in the release surface area, because this polymer has a small transmittance of pheromone. In addition, it is accompanied with the inconvenience that the shape of the controlling agent, for example, bag shape is not suited for aerial application.

In addition, a pest controlling agent made of a biodegradable aliphatic polyester is proposed in Japanese Patent Application Laid-Open No. 6-116103, in which an active ingredient dispersed in a biodegradable polymeric material and then formed into a spherical, film or ribbon-shaped agent is described. In order to disperse the active ingredient in the biodegradable aliphatic polyester, however, a cumbersome step such as film formation using a solvent is necessary. Moreover, the above agent is accompanied with the drawback that the active ingredient dispersed in a biodegradable aliphatic polyester having low affinity therewith tends to cause bleeding without a further treatment.

SUMMARY OF THE INVENTION

An object of the first group of the present invention is to provide a biodegradable sustained-release preparation which can, during application, carry out sustained release of its active ingredient stably at a desired release rate for a long period of time and after application, is degraded by microorganisms even buried in the ground and does not remain in the soil.

The present inventor has found that release of an active ingredient can be controlled easily and all the problems described above can be overcome by mixing 99 to 10 parts by weight of an aliphatic polyester which has a small transmittance of the active ingredient and 1 to 90 parts by weight of a modifier for regulating the sustained release of the enclosed active ingredient, leading to the completion of the first group of the present invention.

In one aspect of the first group of the present invention, there is thus provided a biodegradable sustained-release preparation which comprises a mixture composed of 99 to 10 parts by weight of an aliphatic polyester and 1 to 90 parts by weight of a modifier for the regulation of the sustained releasing property of an active ingredient and the active ingredient held by said mixture.

An object of the second group of the present invention is to provide a reservoir type biodegradable pheromone dispenser which permits, during application, stable sustained release of a pheromone over a long period of time and after application, does not require collection work because of its biodegradability and therefore does not remain in the soil.

Polyester features that an ester linkage in its structure firmly combines molecular chains through a static bond so that it is difficult for pheromone molecules to diffuse the gap of the polymer segment, resulting in a small transmittance of the pheromone in the polyester. The present inventor has found that releasability of a pheromone can be controlled by widening the gap between ester linkages of the main chain structure of an aliphatic polyester and completed the invention of the second group.

In one aspect of the second group of the present invention, there is thus provided a biodegradable pheromone dispenser in which an aliphatic polyester is used as a sustained-release layer for a pheromone contained therein as a liquid phase, said aliphatic polyester having recurring units whose ratio (I/II) of (I) the number of the carbon atoms constituting the main chain and not relating to ester linkage to (II) the number of the carbon atoms constituting the ester linkage is 2 or larger.

An object of the third group of the present invention is to provide a biodegradable pest controlling agent which can be prepared easily, has excellent economical efficiency, permits easy regulation of a release rate or pot life, can satisfy the request for the reduction in the numbers installed or for aerial application, and because of its biodegradability, does not remain in the environment and therefore does not need collection work.

Thee present inventor has carried out an extensive investigation. As a result, it has been found that the above problems can be overcome thoroughly by mixing and dispersing in a biodegradable aliphatic polyester an active ingredient and a carrier,capable of retaining the ingredient at a high content, leading to the completion of the third group of the invention.

In one aspect of the third group of the present invention, there is thus provided a biodegradable pest controlling agent obtained by mixing and dispersing in a biodegradable aliphatic polyester an active ingredient and a carrier retaining the active ingredient therein.

In another aspect of the third group of the invention, there is also provided a biodegradable pest controlling agent which is a composition comprising 2 to 60 wt. % of an active ingredient, 30 to 95 wt. % of a biodegradable aliphatic polyester and 2 to 50 wt. % of a carrier retaining the active ingredient.

BRIEF DESCRIPTION OF THE DRAWINGS

FIG. 2 is a perspective view illustrating an embodiment of a bag-shaped dispenser among the dispensers according to the second group of the present invention;

DESCRIPTION OF THE PREFERRED EMBODIMENTS

Figure 1:
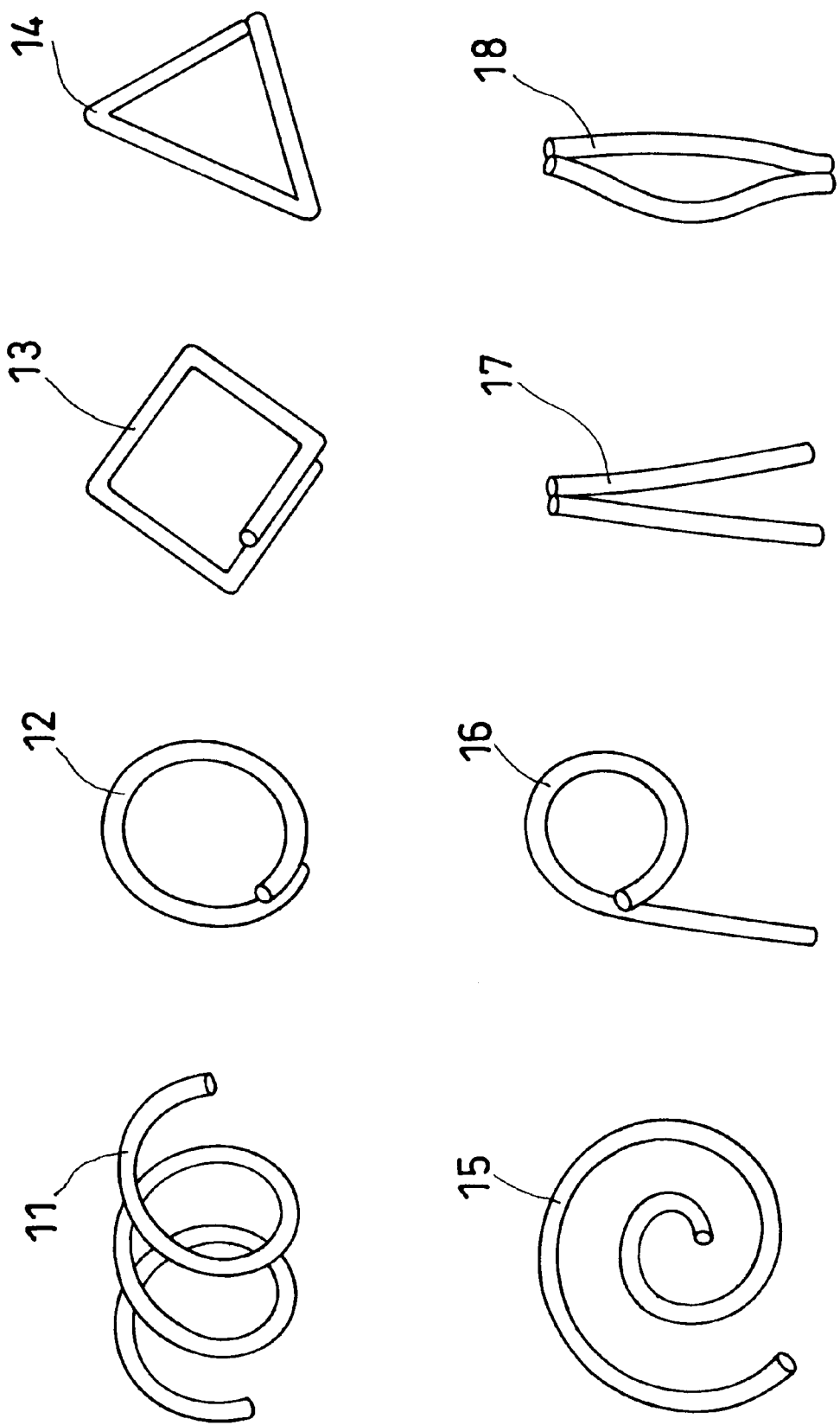
FIG. 1 is a schematic view illustrating an embodiment of a tube-shaped dispenser among the dispensers according to the second group of the present invention.

1. Biodegradable Sustained-release Preparation (according to the first group of the invention)

As a mixture for holding an active ingredient of the sustained-release preparation according to the first group of the present invention, employed is a mixture comprising 99 to 10 parts by weight of an aliphatic polyester and 1 to 99 parts by weight (when no other components are contained, the above weight part can be replaced by wt. %) of a modifier for regulating the releasability of the active ingredient held therein. When the amount of the modifier is smaller than 1 part by weight relative to 99 to 10 parts by weight of the aliphatic polyester, the modifier does not exhibit its effects. When the amount of the aliphatic polyester is smaller than 10 parts by weight relative to 1 to 90 parts by weight of the modifier, on the other hand, no biodegradation effects can be expected. The mixture for holding the active ingredient is more preferred to contain the modifier at a concentration falling within a range of from 5 to 60 wt. %.

No particular limitation is imposed on the above-described aliphatic polyester insofar as it has biodegradability. Specific examples include condensation and polymerization products between a $C_{2-20}$ carboxylic acid such as malonic acid, succinic acid, succinic anhydride, glutaric acid, adipic acid, adipic anhydride, sebacic acid, fumaric acid, maleic acid, didodecanoic acid, malic acid, tartaric acid or citric acid and a $C_{2-20}$ alcohol such as ethylene glycol, propylene glycol, butane diol, hexane diol, octane diol, decane diol, cyclohexane dimethanol, glycerin, or trimethylol propane; ring-opening polymerization products of a cyclic ester such as lactide, which is a cyclic dimer of lactic acid, or caprolactone; condensation and polymerization products of a hydroxy acid such as lactic acid, hydroxybutyric acid or hydroxyvaleric acid. The above exemplified aliphatic polyesters can be used either singly or in combination.

As a modifier for regulating the sustained releasability of an active ingredient, any modifiers having an equilibrium swelling ratio at 40° C. of at least 2 wt. % can be used. The term "equilibrium swelling ratio" as used herein means an equilibrium swelling ratio at 40° C. Represented by the following formula:

$$\text{Equilibrium swelling ratio} = \frac{(\text{Weight of swelling sample}) - (\text{Weight of dry sample})}{\text{Weight of dry sample}} \times 100$$

Examples of such a modifier include natural high polymers such as cellulose, chitin, chitosan, pullulan and polyamino acid, and derivatives thereof; and synthetic high polymers such as polyvinyl alcohol, polyethylene glycol, polyurethane, polyamide and polyolefins, e.g. polyethylene, polypropylene and polystyrene, and derivatives thereof. From the viewpoint of the miscibility with an aliphatic polyester and modifying effects of the sustained releasability of an active ingredient, desired are poly-ϵ-caprolactone, polyvinyl acetate, ethylene-vinyl acetate copolymer, ethylene-ethyl acrylate copolymer, polyvinyl chloride, polymethacrylate ester and cellulose derivatives such as cellulose triacetate and cellulose acetate butyrate, and mixtures thereof. Concerning the ethylene-vinyl acetate copolymer, that having a vinyl acetate content of 4 to 90% is suitably used.

Any substance having physiological activities such as attracting activity, repellent activity and aromatic activity and pesticidal activities such as insecticidal activity can be employed as the active ingredient of the first group of the present invention without particular limitation.

Specific examples of the active ingredient having attracting activity include Z-7-dodecenyl acetate, Z-8-dodecenyl acetate, Z-9-dodecenyl acetate, E,Z-7,9-dodecadienyl acetate, Z,Z-7,9-dodecadienyl acetate, E,E-8,10-dodecadienol, E-4-tridecenyl acetate, Z-9-tetradecenyl acetate, Z-9-tetradecenal, Z-11-tetradecenyl acetate, Z-11-tetradecenal, Z-9-hexadecenal, Z-11-hexadecenal, Z, E-9,11-tetradecadienyl acetate, Z, E-9,12-tetradecadienyl acetate, Z-11-hexadecenyl acetate, Z,Z-7,11-hexadecadienyl acetate, Z, E-7,11-hexadecadienyl acetate, E,E, Z-4,6,10-hexadecatrienyl acetate, E,E-10,12-hexadecadienal, Z,Z-3,13-octadecadienyl acetate, E,Z-3,13-octadecadienyl acetate, Z-7,8-epoxy-2-methyl-octadecene, Z-13-icosen-10-on, E,E, Z-10,12,14-hexadecatrienyl acetate, E,E, Z-10,12,14-hexadecatrienal, Z-10-tetradecenyl acetate, E, Z-4,10-tetradecadienyl acetate, 14-methyl-1-octadecene, (R,Z)-5-(1-octenyl)oxacyclopentan-2-on, (R,Z)-5-(1-decenyl) oxacyclopentan-2-on and (R,Z)-5-(1-decenyl) oxacyclopentan-2-on. These compounds are known as pheromones and are composed of a $C_{10-20}$ unsaturated aliphatic hydrocarbon, acetate, aldehyde, alcohol, ketone or epoxy compound. They can be used either singly or in combination.

Examples of the active ingredient having repellent activity include triethylene glycol monohexyl ether and N, N-diethyl-m-triamide. Examples of the active ingredient having aromatic activity include geraniol, limonene, benzyl alcohol, esters of a $C_{6-20}$ hydrocarbon, ethers, aldehydes and alcoholic compounds. Examples of the active ingredient having pesticidal activity include insecticides such as salithion, diazinon and chlorpyrifos and bactericides such as thiophanate-methyl and captan.

No particular limitation is imposed on the shape for holding the active ingredient. In other words, there are various forms for holding the active ingredient by a holding mixture. Specific examples include microcapsules in which the surface of the active ingredient has been covered with the holding mixture; and products processed into a desired shape, each being obtained by kneading the active ingredient in the holding mixture or forming a uniform solution of the holding mixture and the active ingredient, dispersing the active ingredient in the holding mixture by the removal of the solvent or the like and then processing the dispersion into a desired shape such as sphere, sheet, film, rod, pipe, thread, tape or chip. In addition, these processed products having a surface covered with a barrier layer for controlling the release of the active ingredient and those coated with an adhesive for improving applicability can be given as examples. As further examples, those obtained by filling the active ingredient in the holding mixture processed into a form of a capillary tube, heat sealing both ends of the capillary tube and then encapsulating the active ingredient therein; and those obtained by centrally cutting the above-mentioned capillary tube into two pieces, thereby having each one end as an opening.

The container formed of a holding mixture which container has an active ingredient enclosed therein as a liquid phase is more preferred in order to secure uniform releasability over a long period of time. As such shape, tube-, bottle- or bag-shaped container is used preferably.

The active ingredient hold as a liquid phase in such a container transmits through a sustained-release layer constituting the preparation, thereby being released. When the holding mixture is formed into a container and the active ingredient is enclosed therein, the sustained release layer means the wall of the container itself.

When the mixture is formed into a container, the sustained release layer desirably has a thickness of at least 0.02 mm for effecting stable sustained release. The thickness smaller than 0.02 mm is not preferred because it causes pinholes or excess release of the active ingredient such as pheromone. There occurs no particular problem when the sustained release layer has a thickness not smaller than 0.02 mm, but that ranging from 0.05 mm to 5 mm is more preferred. When it exceeds 5 mm, the release amount of a pheromone tends to become too small.

The release surface area of the sustained release preparation formed of such a container is desirably 1 cm$^2$ or larger. Surface areas smaller than 1 cm$^2$ make it difficult to secure a sufficient release amount and are therefore not suited. No particular problem occur when the release surface area is 1 cm$^2$ or larger, but a range of from 2 cm$^2$ to 2 m$^2$ is more preferred. Surface areas exceeding 2 m$^2$ are not practical because it is difficult to install the preparation having such a large surface area.

When the active ingredient is enclosed and held in a container of the sustained release preparation, said container having been formed of a holding mixture, it may be enclosed in portions. The enclosed amount is preferably at least 1 mg, more preferably at least 5 mg. It is difficult to enclose the ingredient in an amount less than 1 mg.

As the shape of the container formed of a holding mixture, a tube, bottle and bag are preferred. In the case of the tube-shaped preparation, that having an internal diameter of 0.4 mm to 10 mm is preferred. Internal diameters smaller than 0.4 mm make it difficult to fill the active ingredient in the container, while those larger than 10 mm make it difficult to conduct encapsulation. The bottle-shaped preparation is formed by blow molding or injection molding and preferred is that having an internal volume of 0.1 to 200 ml. The bottle having an internal volume less than 0.1 ml cannot be formed easily, while that having an internal volume greater than 200 ml is not economical because there is a large difference between the amount of the active ingredient filled therein and the internal volume. In the case of a bag-shaped preparation, the amount of the active ingredient filled in the bag is desirably 1 mg to 100 g. Neither amounts smaller than 1 mg nor exceeding 200 g are preferred because it is difficult to fill such an amount in the bag.

The biodegradable sustained-release preparation according to the first group of the present invention should retain its essential performance during application so that a pigment or dye, or various stabilizers such as ultraviolet absorber or antioxidant may be added to the holding mixture in order to improve the weather resistance. Alternatively, it is possible to add such an additive to the active ingredient enclosed in the container formed of a holding mixture.

Examples of the first group of the present invention will hereinafter be given but it should however be borne in mind that the fist group of the present invention is not limited to or by these examples.

EXAMPLE 1

In a twin roll, a polycondensate (product of Showa Highpolymer Co., Ltd.) composed of 1,4-butanediol and a 4:1 mixture of succinic acid and adipic acid was mixed with 60 wt. % of poly-$\epsilon$-caprolactone (product of Union Carbide Corp.) at 100° C. The sample so obtained was heat sealed at 130 ° C. for 5 minutes, whereby a sheet having a thickness of 0.2 mm was produced. The sheet was formed into a bag of 20 mm in width and 25 mm in length, which was filled with 100 mg of Z-11-hexadecenal, which was a sex hormone of diamond black moth (*Plutella xylostella*). The release rate of Z-11-hexadecenal from the sustained-release preparation so obtained was measured under the conditions at 30° C. and 1 m/s. As a result, it continued uniform release at 2.1 mg/day for about 40 days and therefore had excellent stable releasability over a long period of time.

When the above sustained-release preparation was buried in the ground from April to October, it was worn out and degradation proceeded even to cause disappearance of a portion of it.

The equilibrium swelling ratio at 40° C. of poly-$\epsilon$-caprolactone (product of Union Carbide Corp.), which was used as a modifier, to Z-11-hexadecenal-was 8.3 wt. %.

COMPARATIVE EXAMPLE 1

In a similar manner to Example 1 except that only a polycondensate (product of Showa Highpolymer Co., Ltd.) composed of 1,4-butanediol and a 4:1 mixture of succinic acid and adipic acid was used, a sustained-release preparation was prepared. As a result of the evaluation of the release rate of the preparation so obtained, it continued uniform release at 0.9 mg/day for about 100 days. In order to secure the similar release rate to Example 1, however, at least twice the amount of the sustained-release preparation was necessary. In addition, owing to a small release rate, a large amount of the active ingredient remained even after the expiration of the necessary period so that the preparation in Comparative Example 1 was not suited for practical use.

EXAMPLE 2

In a twin roll, a polycondensate (product of Showa Highpolymer Co., Ltd.) composed of 1,4-butanediol and succinic acid was mixed with 30 wt. % of poly-$\epsilon$-caprolactone (product of Union Carbide Corp.) at 120° C. The sample so obtained was heat sealed at 150° C. for 5 minutes, whereby a sheet having a thickness of 0.2 mm was produced. The sheet was formed into a bag of 25 mm in width and 30 mm in length, which was filled with 100 mg of E,E-8,10-dodecadienol, which was a sex hormone of codlin moth (*Cydia pomonella*). The release rate of E,E-8, 10-dodecadienol from the sustained-release preparation so obtained was measured under the conditions at 30° C. and 1 m/s. As a result, it continued uniform release at 1.7 mg/day for about 50 days and therefore had excellent stable releasability over a long period of time.

When the sustained-release preparation was buried in the ground from April to October, it partially disappeared and degradation proceeded even to lose original shape.

The equilibrium swelling ratio at 40° C. of poly-$\epsilon$-caprolactone (product of Union Carbide Corp.), which was used as a modifier, to E,E-8,10-dodecadienol was 8.9 wt. %.

COMPARATIVE 2

In a similar manner to Example 2 except that only a polycondensate (product of Showa Highpolymer Co., Ltd.) composed of 1,4-butanediol and succinic acid was used, a sustained-release preparation was prepared. As a result of the evaluation of the release rate of the preparation so obtained, it continued uniform release at 0.6 mg/day for about 150 days. In order to secure the similar release rate to Example 2, however, at least three times the amount of the sustained-release preparation was necessary. In addition, owing to a small release rate, a large amount of the active ingredient remained even after the expiration of the necessary period so that the preparation in Comparative Example 2 was not suited for practical use.

EXAMPLE 3

In a twin roll, polylactic acid (product of Cargill Corp.) was mixed with 40 wt. % of poly-ε-caprolactone (product of Union Carbide Corp.) at 150° C. The sample so obtained was heat sealed at 160° C. for 5 minutes, whereby a sheet having a thickness of 0.3 mm was produced. The sheet was formed into a bag of 20 mm in width and 25 mm in length, which was filled with 90 mg of Z-11-tetradecenyl acetate, which was a sex hormone of a leaf folder. The release rate of Z-11-tetradecenyl acetate from the sustained-release preparation so obtained was measured under the conditions at 30° C. and 1 m/s. As a result, it continued uniform release at 1.9 mg/day for about 40 days and therefore had excellent stable releasability over a long period of time.

When the sustained-release preparation was buried in the ground from April to October, the end portion of it disappeared and the preparation itself became considerably fragile and was degraded to an easily cracked extent.

The equilibrium swelling ratio at 40° C. of poly-ε-caprolactone (product of Union Carbide Corp.), which was used as a modifier, to Z-11-tetradecenyl acetate was 7.1 wt. %.

COMPARATIVE EXAMPLE 3

In a similar manner to Example 3 except that only polylactic acid (product of Cargill Corp.) was used, a sustained-release preparation was produced. As a result of the evaluation of the release rate, the preparation showed a release rate of only 0.01 mg/day and was therefore not suited for practical use.

COMPARATIVE EXAMPLE 4

In a similar manner to Example 3 except that only 0.5 wt. % of poly-ε-caprolactone (product of Union Carbide Corp.) was mixed, a sustained-release preparation was produced. As a result of the evaluation of the release rate, the preparation showed a release rate of only 0.01 mg/day and no modifying effect was observed.

COMPARATIVE EXAMPLE 5

To polylactic acid (product of Cargill Corp.), 30 wt. % of a polycondensate (product of Showa Highpolymer Co., Ltd.) composed of 1,4-butanediol and a 4:1 mixture of succinic acid and adipic acid were added and in a twin roll, they were mixed at 150° C. whereby a sample was prepared. Using the sample, a sustained-release preparation was produced in a similar manner to Example 3. As a result of the evaluation of the release rate, the preparation showed a release rate of only 0.04 mg/day and no modifying effect was observed.

Incidentally, the equilibrium swelling ratio at 40° C. of the polycondensate (Showa Highpolymer) composed of 1,4-diol and a 4:1 mixture of succinic acid and adipic acid to Z-11-tetradecenyl acetate was 0.8 wt. %.

EXAMPLE 4

To a polycondensate (product of Showa Highpolymer Co., Ltd.) composed of 1,4-butanediol and a 4:1 mixture of succinic acid and adipic acid, which had been used in Example 1, 40 wt. % of an ethylene-vinyl acetate copolymer (product of Mitsubishi Chemical; a vinyl acetate content: 15 wt. %) were added. In a twin roll, they were mixed at 100° C. The sample so obtained was heat sealed at 130° C. whereby a sheet having a thickness of 0.2 mm was produced. The sheet was formed into a bag of 20 mm in width and 20 mm in length, which was filled with 90 mg of Z-11-tetradecenyl acetate in a similar manner to Example 3. The release rate of Z-11-tetradecenyl acetate from the sustained-release preparation so obtained was measured under the conditions at 30° C. and 1 m/s. As a result, it continued uniform release at 2.0 mg/day for about 40 days and therefore had excellent stable releasability over a long period of time.

When the sustained-release preparation was buried in the ground from April to October, it partially disappeared and was considerably worn out.

The equilibrium swelling ratio at 40° C. of the ethylene-vinyl acetate copolymer (product of Mitsubishi Chemical Co., Ltd.; a vinyl acetate content: 15 wt. %), which was used as a modifier, to Z-11-tetradecenyl acetate was 29.1 wt. %.

COMPARATIVE EXAMPLE 6

In a similar manner to Example 4 except that 91 wt. % of an ethylene-vinyl acetate copolymer (product of Mitsubishi Chemical Co., Ltd.; a vinyl acetate content: 15 wt. %) was added, a sustained-release preparation was produced. As a result of the evaluation of the release rate, the preparation showed uniform release at 3.1 mg/day for about 20 days but it was accompanied with the inconvenience that the pheromone oozed out on the surface of the preparation and became sticky.

When the sustained-release preparation so obtained was buried in the ground from April to October, no apparent change was observed and biodegradation did not occur.

COMPARATIVE EXAMPLE 7

In a similar manner to Example 4, the release rate of "Hamakicon" (trade name; product of Shin'etsu Chemical Co., Ltd.) which was a mating disruption agent of a leaf folder was evaluated. As a result, it showed uniform release at 1.9 mg/day for about 35 days and after that, the release rate showed a gradual decrease.

In addition, the preparation was buried in the ground from April to October but no change was observed.

EXAMPLE 5

To a polycondensate (product of Showa Highpolymer Co., Ltd.) composed of 1,4-butanediol and a 4:1 mixture of succinic acid and adipic acid, which was similar to that used in Example 1, 30 wt. % of an ethylene-ethylene acrylate copolymer (product of Nippon Unicar Co., Ltd.; an ethyl acrylate content of 10%) were added. They were mixed at 100° C. in a twin roll. The sample so obtained was pelletized by a sheet pelletizer, followed by the formation of a capillary tube having an internal diameter of 0.8 mm and a wall thickness of 0.5 mm by an extruder. The capillary tube so formed was filled with Z,Z/E-7,11-hexadecadienyl acetate, which was a sex pheromone of *Pectinophora gossypiella* and then heat sealed at every 20 cm length, whereby a sustained-release preparation was produced.

The release rate from the sustained-release preparation so obtained was measured under the conditions at 30° C. and 1 m/s. As a result, the preparation continued release at 0.8 mg/day for about 70 days and was therefore excellent in the stable release over a long period of time.

When the preparation so obtained was buried in the ground from April to October, it retained its shape but was covered with mold on the surface and was easily worn out. Thus, an advance of biodegradation was observed.

The equilibrium swelling ratio at 40° C. of the ethylene-ethyl acrylate copolymer (product of Nippon Unicar Co., Ltd.; an ethyl acrylate content of 10%), which was used as a modifier, to Z,Z/E-7,11-hexadecadienyl acetate was 18.4 wt. %.

COMPARATIVE EXAMPLE 8

In a similar manner to Example 5, "PB-Rope" (trade name; product of Shin-Etsu Chemical Co., Ltd.), which was a mating disruption agent for Pectinophora gossypiella was evaluated. As a result, the preparation continued uniform release at 0.8 mg/day for about 70 days, which was equivalent to the case of Example 5.

When the above sustained-release preparation was buried in the ground from April to October, no apparent change was observed. It was not torn to pieces even if drawn by hands and no degradation occurred.

EXAMPLE 6

To a polycondensate (product of ZENECA K.K.) of 3-hydroxyacetic acid and hydroxyvaleric acid, 30 wt. % of poly-$\epsilon$-caprolactone (product of Union Carbide Corp.) were added. They were mixed at 140° C. in a twin roll. The sample so obtained was pelletized by a sheet pelletizer, followed by the formation of a capillary tube having an internal diameter of 0.8 mm and wall thickness of 0.5 mm by an extruder. The capillary tube so formed was filled with Z-8-dodecenyl acetate, which was a sex pheromone of *Grapholita molesta* and was heat sealed and cut at every 20 cm, whereby a sustained-release preparation was produced.

The release rate from the sustained-release preparation was measured under the conditions at 30° C. and 1 m/s. As a result, the preparation continued uniform release at 1.6 mg/day for about 40 days and was excellent in the stable release over a long period of time.

When the above sustained-release preparation was buried in the ground from April to October, it barely retained its shape and was considerably fragile. It was degraded to an extent easily torn into pieces by hands.

The equilibrium swelling ratio at 40° C. of poly-$\epsilon$-caprolactone (product of Union Carbide Corp.), which was used as a modifier, to Z-8-dodecenyl acetate was 9.9 wt. %.

EXAMPLE 7

To poly-$\epsilon$-caprolactone (product of Union Carbide Corp.), 10 wt. % of polyvinyl acetate (product of Aldrich Chemical Co., Inc.) were added. They were mixed at 90° C. in a twin roll. The sample so obtained was pelletized by a sheet pelletizer, followed by the formation of a bottle having a thickness of 2 mm, an internal volume of 5 ml and outer surface area of 25 cm$^2$ by a blow molder.

The bottle was filled with 1 g of Geraniol having a rose odor, followed by heat sealing of an inlet opening, whereby a sustained-release preparation was produced. When the sustained-release preparation so obtained was placed inside of a room, it emitted a rose odor over about 2 months. The result was therefore satisfactory.

When the above sustained-release preparation was buried in the ground from April to October, it retained its shape but was covered with mold and decreased in weight by 9%. Thus, progress of the biodegradation by microorganisms was observed.

The equilibrium swelling ratio at 40° C. of polyvinyl acetate (product of Aldrich Chemical Co., Inc.), which was used as a modifier, to geraniol was 12.9 wt. %.

As can be understood from the above description, the use of the sustained-release preparation according to the first group of the present invention makes it possible to release the active ingredient stably over a long period of time, thereby maintaining its effects for a long time. It is also possible to secure a large release rate of the active ingredient, which makes it possible to reduce the size of the preparation and reduce the number of the preparations to be placed, leading to the cost reduction. Moreover, owing to the biodegradability, the preparation is free from collection after application and is therefore labor saving in agricultural applications. It is also useful from the viewpoint of the environmental protection, because it is degraded by microorganisms and does not remain in the soil.

2. Biodegradable Pheromone Dispenser (according to the second group of the invention)

In the second group of the present invention, employed as a sustained-release layer of a pheromone is an aliphatic polyester wherein in the recurring units forming a polymer, a ratio (I/II) of (I) the number of the carbon atoms constituting the main chain and not relating to the ester linkage to (II) the number of the carbon atoms constituting the ester linkage is 2 or larger.

The term "(I) the number of the carbon atoms constituting the main chain and not relating to the ester linkage" as used herein means the number of carbon atoms other than those forming an ester linkage in the main chain structure and does not contain the number of carbon atoms of the side chain. The term "a ratio (I/II) of (I) the number of the carbon atoms constituting the main chain to (II) the number of the carbon atoms constituting the ester linkage" as used herein means a value of one of the recurring units forming the polymer and in the case of a polyester having at least three monomers, it means weighted mean of the respective recurring units according to these monomer compositions. In other words, it means the total of the values obtained by multiplying a ratio (I/II) of each monomer by the proportion of each monomer composition supposing that the whole composition is 1.

For example, in the case of an aliphatic polyester having the following recurring units, the number (I) of the carbon atoms of the main chain is the sum total of (a) parts and the number (II) of the carbon atoms forming an ester linkage is the sum total of (b) parts.

The number (I) of carbon atoms forming the main chain:

$$(I)=(4+2)\times 0.8+(4+4)\times 0.2=6.4$$

The number (II) of carbon atoms constituting an ester linkage $$(II)=2\times 0.8+2\times 0.2=2$$

Accordingly, the ratio (I/II)=6.4/2=3.2

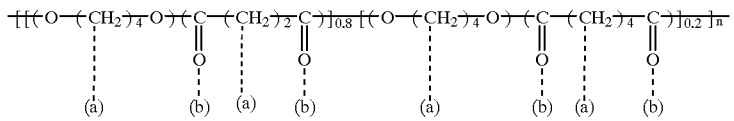

Examples of such an aliphatic polyester include condensation and polymerization products between a $C_{2-20}$ carboxylic acid such as malonic acid, succinic acid, succinic anhydride, glutaric acid, adipic acid, adipic anhydride, sebacic acid, fumaric acid, maleic acid, didodecanoic acid, malic acid, tartaric acid or citric acid and a $C_{2-20}$ alcohol such as ethylene glycol, propylene glycol, butanediol, hexanediol, octanediol, decanediol, cyclohexane dimethanol, glycerin, or trimethylol propane; and ring-opening polymers of a cyclic ester such as E-caprolactone.

As such an aliphatic polyester, those having a side chain may be used, but it is necessary that the ratio (I/II) of the number (I) of the carbon atoms constituting the main chain and not relating to an ester linkage to the number (II) of the carbon atoms forming the ester linkage is at least 2. When the ratio (I/II) is smaller than 2, the static bond of the polymer segment becomes firmer, which lowers the transmission of a pheromone, thereby making impossible to maintain a release rate necessary for the pest control. No particular limitation is imposed on the ratio of (I/II) insofar as it is not smaller than 2, but the ratio of 20 or smaller is preferred for preventing excessive release of a pheromone.

The aliphatic polyester may be a single composition such as ring-opening polymerization product or may be a polycondensate composed of a dicarboxylic acid and a diol derivative. An aliphatic polyester composed of at least three monomer units is however preferably used to properly control the release performance of a pheromone. It may be a random copolymer or may have a structure of a block copolymer available by coupling or the like. An aliphatic polyester obtained by polymer blend of at least three monomer units may also be used.

No particular limitation is imposed on the shape of a dispenser, but a reservoir type having therein a pheromone as a liquid phase is preferred. It is desired that this dispenser encapsulates a pheromone therein and is not equipped with an opening such that the pheromone is brought in direct contact with the outside air. As a container satisfying the above condition, tube-, bottle- and bag-shaped containers are suited. Obviously, these containers may additionally have a jig such as stick or attachment for attaching the pheromone to a material to be treated such as crops. In such a reservoir type dispenser, the wall surface of the reservoir itself constitutes a sustained release layer of a pheromone.

The pheromone held by a liquid phase transmits through a sustained release layer forming a preparation and is released. For the stable sustained release, thickness of at least 0.02 mm is necessary. The thickness smaller than 0.02 mm is not suited because it causes pinholes or excessive release of the active ingredient such as pheromone. There occurs no particular problem when the sustained release layer has a thickness not smaller than 0.02 mm, but that ranging from 0.05 mm to 5 mm is more preferred. When it exceeds 5 mm, the release amount of a pheromone tends to become too small, which requires much widening of a release area. So, such a thickness is not suited for practical use.

The release surface area of the sustained release preparation is required to be 1 cm$^2$ or larger. Surface areas smaller than 1 cm$^2$ make it difficult to secure a sufficient release amount for pest control and are therefore not suited. No particular problem occurs when the release surface area is 1 cm$^2$ or larger, but a range of from 2 cm$^2$ to 2 m$^2$ is more preferred. Surface areas exceeding 2 m$^2$ are not practical because it is difficult to attach the preparation having such a large surface area.

The pheromone to be enclosed in a dispenser may be encapsulated in portions. The encapsulated amount is preferably at least 1 mg, more preferably at least 5 mg. It is difficult to encapsulate an amount less than 1 mg in the dispenser.

As the dispenser, a tube-, bottle- and bag-shaped containers are preferred. In the case of the tube-shaped container, that having an internal diameter of 0.4 mm to 10 mm is preferred. Internal diameters smaller than 0.4 mm make it difficult to fill the pheromone in the container, while those larger than 10 mm make it difficult to conduct encapsulation. The bottle-shaped preparation is formed by blow molding or injection molding and preferred is that having an internal volume of 0.1 to 200 ml. The bottle having an internal volume less than 0.1 ml cannot be formed easily, while that having an internal volume greater than 200 ml is not economical because there is a large difference between the amount of the pheromone filled therein and the internal volume. In the case of a bag-shaped preparation, the amount of the pheromone filled in the bag is desirably 1 mg to 100 g. Neither amounts smaller than 1 mg nor exceeding 100 g are preferred because it is difficult to fill such an amount in the bag.

The pheromone dispenser is required to have means to attach the dispenser to a material to be treated such as crops and means known to date can be employed for it.

As a tube-shaped dispenser, dispensers having a metal wire installed thereto and having shapability are given as examples. Described specifically, exemplified is a tube-shaped container produced by disposing a metal wire along a longitudinal direction of the main body of the container, covering the metal wire with a resin material forming the container and then integrating the body and the wire by molding.

Any material can be employed as the metal wire because it has no influence on the performance of the pheromone dispenser. It is desired to use a material which tends to cause oxidation and deterioration such as iron wire so as not to impair the characteristics of the biodegradability.

Furthermore, the pheromone dispenser according to the present invention is desired to have, in advance, a shape permitting the attachment to a material to be treated.

FIG. 1 illustrates a shape feasible as a tube-shaped dispenser. In this dispenser, a tube-shaped reservoir containing a pheromone therein is folded or bent into a proper shape. A spiral-shaped, a ring-shaped, square-shaped and triangle-shaped dispensers are indicated at numerals 11, 12, 13 and 14, respectively. It is also possible to form into other polygonal shapes or even to form into a star shape. Indicated at numerals 15 and 16 are swirl shape and 9 shape. In addition, a pine needle shape in which plural tubes are linked at their one end as indicated at numeral 17 and a cyclic tube in which plural tubes are linked and integrated at their both ends as shown at numeral 18 can be exemplified.

In addition, as illustrated in FIG. 2, bottle-shaped or bag-shaped dispensers can be formed as those having a hook or cyclic filament connected therewith.

In FIG. 2, illustrated at numeral 21 is a dispenser equipped with a hook portion 22. This dispenser 21 has a bag-shaped portion 23 for storing a pheromone therein. In this dispenser, the bag-shaped portion 23 is formed by laminating two aliphatic polyester films constituting a sustained release layer and the hook portion 22 can be formed integrally with the bag-shaped portion by using the same material.

Illustrated at 31 is a dispenser equipped with a hook portion 32 of another shape and it has a bag-shaped portion 33. It is similar to the above dispenser 21 in the basic structure.

Illustrated at 41 is a dispenser equipped with a hook portion 42 of a further shape and has a bag-shaped portion 43. It is similar to the above dispenser 21 in the basic structure.

Illustrated at 51 is a dispenser equipped with a filament portion 52 of a still further shape and has a bag-shaped portion 53. It is similar to the above dispenser 21 in the basic structure.

Incidentally, the above bag-shaped portions 23, 33, 43 and 53 can be replaced by bottle-shaped portions.

Figure 3:
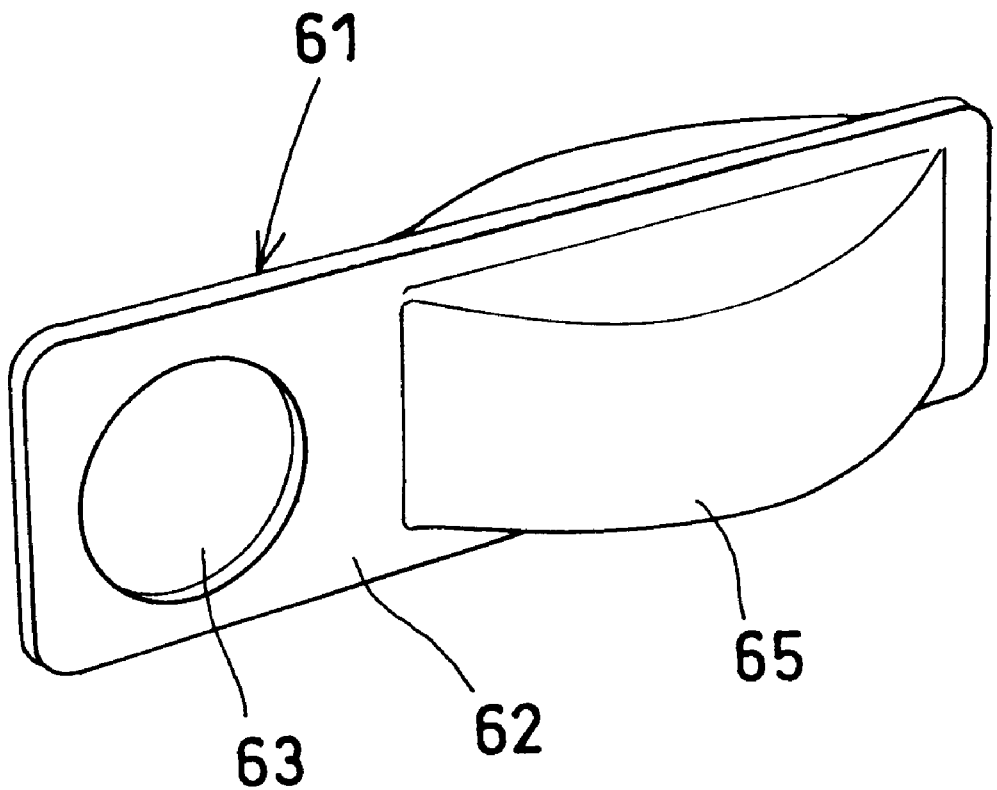
FIG. 3 is a perspective view illustrating another embodiment of a bag-shaped dispenser among the dispensers according to the second group of the present invention.

Another bag-shaped dispenser, as illustrated in FIG. 3, is a dispenser 61 in which aliphatic polyester films are laminated each other to form a bag and a hole 63 is made in the laminated film 62. Upon application, an end 64 far from the hole is inserted into the hole 63, whereby the dispenser can be wound round a material to be treated such as branch. This dispenser 61 has a storing bag 65 for enclosing a pheromone therein.

No particular limitation is imposed on the pheromone usable in the present invention. Any pheromone such as alarm pheromone, trail marking pheromone or class differentiation pheromone can be used but a sex pheromone is suited to carry out pest control efficiently. Known examples of the sex hormone include unsaturated aliphatic hydrocarbons having 10 to 20 carbon atoms, acetates, aldehydes, alcohols, ketones and epoxy compounds. In general, they may be used either singly or in combination. More specifically, those exemplified as the active ingredient in the first group of the present invention can be employed.

The sustained-release layer of the biodegradable pheromone dispenser according to the second group of the present invention should retain its essential performance during application so that a pigment or dye, or various stabilizers such as ultraviolet absorber or antioxidant may be added to it in order to improve the weather resistance.

EXAMPLE 8

A sheet of 0.1 mm thick was formed by hot pressing a polycondensate (product of Showa Highpolymer Co., Ltd.) composed of 1,4-butanediol and a 4:1 mixture of succinic acid and adipic acid at 130° C. for 5 minutes. The sheet was formed into a bag of 20 mm in width and 30 mm in length, which was filled with 90 mg of Z-11-tetradecenyl acetate, which was a sex hormone of a leaf folder.

The release rate of Z-11-teteradecenyl acetate from the dispenser so formed was measured under the conditions at 30° C. and 1 m/s. As a result, the dispenser continued uniform release at 2.0 mg/day for about 40 days and therefore had excellent releasability.

The release surface area of the dispenser was 12 cm$^2$. In the aliphatic polyester, the ratio (I/II) of the carbon atoms (I) constituting the main chain and not relating to ester linkage to the carbon atoms (II) constituting the ester linkage was 3.2

When the above dispenser was buried in the ground from April to October, it was worn out and almost lost its original form.

COMPARATIVE EXAMPLE 9

A sheet of 0.1 mm thick was formed by hot pressing polylactic acid (product of Cargill Corp.) at 160° C. for 5 minutes. In a similar manner to Example 8, the release rate of Z-11-tetradecenyl acetate was measured. As a result, it showed a release rate of only 0.1 mg/day or so and was not suited for practical use. The ratio (I/II) of the aliphatic polyester was 1.0.

COMPARATIVE EXAMPLE 10

A sheet of 0.1 mm thick was formed by hot pressing a polycondensate (product of ZENECA K.K.) between 3-hydroxybutyric acid and 3-hydroxyvaleric acid at 160° C. for 5 minutes. In a similar manner to Example 8, the release rate of Z-11-tetradecenyl acetate was measured. As a result, it showed only a release rate of about 0.5 mg/day and was found not suited for practical use. The ratio (I/II) of the aliphatic polyester was 2.0.

COMPARATIVE EXAMPLE 11

In a similar manner to Example 8, the release rate of "Hamakikon" (trade name; product of Shin'etsu Chemical Co., Ltd.) which was a mating disruption agent of a leaf folder was measured at 30° C. and 1 m/s. As a result, it showed uniform release at 1.9 mg/day for about 35 days but after that, the release rate showed a gradual decrease.

The above dispenser was buried in the ground from April to October but no change was observed.

EXAMPLE 9

A tube having an internal diameter of 0.8 mm and a wall thickness of 0.5 mm was formed by extruding the aliphatic polyester as employed in Example 8. The tube so formed was filled with Z-8-dodecenyl acetate, which was a sex pheromone of *Grapholita molesta*, and heat sealed and cut at every 20 cm, whereby a pheromone dispenser having Z-8-dodecenyl acetate encapsulated therein was obtained. The release rate from the dispenser was measured under the conditions at 30° C. and 1 m/s. As a result, the dispenser continued uniform release at 1.9 mg/day for about 35 days and was found to be suited for practical use.

Incidentally, the release surface area of the above dispenser was 11 cm$^2$.

EXAMPLE 10

A film of 0.06 mm thick was formed by T-die extrusion of, as an aliphatic polyester, a polycondensate (product of Showa Highpolymer Co., Ltd.) composed of 1,4-butanediol and a 4:1 mixture of succinic acid and adipic acid. The sheet was formed into a bag of 25 mm in width and 30 mm in length, followed by filling with 100 mg of E,E-8,10-dodecadienol, which was a sex hormone of codlin moth (*Cydia pomonella*), whereby a dispenser was obtained.

The release rate from the dispenser so obtained was measured under the conditions at 30° C. at 1 m/s. As a result, it continued uniform release at 1.4 mg/day for about 65 days and therefore was found to be suited for practical use.

Incidentally, the release surface area of the dispenser was 15 cm². The ratio (I/II) of the aliphatic polyester was 3.0.

When the dispenser was buried in the ground from April to October, it was worn out and a portion of it had already disappeared.

COMPARATIVE EXAMPLE 12

In a similar manner to Example 10 except that a film of 0.01 mm thick was used instead, a pheromone dispenser was obtained.

The release rate from the dispenser was measured under the conditions at 30° C. and 1 m/s. As a result, it showed excessive release of 5.4 mg/day and the pheromone oozed out on the surface of the dispenser and became sticky. The dispenser was therefore found not suited as a pheromone dispenser.

EXAMPLE 11

A bottle having a thickness of 1 mm, an internal volume of 0.5 ml and an outer surface area of about 8 cm² was formed by blow molding of poly-ε-caprolactone (product of Union Carbide Corp.). The bottle so formed was filled with 100 mg of a 1:1- mixture of Z-11-hexadecenyl acetate and Z-11-hexadecenal which mixture was a sex pheromone of diamond black moth (*Plutella xylostella*), whereby a pheromone dispenser was obtained. The release rate from this dispenser under the conditions at 30° C. and 1 m/s was measured. As a result, the dispenser continued uniform release for about 55 days at 1.5 mg/day and was found to be suited for practical use.

The ratio (I/II) of the aliphatic polyester was 5.0.

The above dispenser was buried in the ground from April to October. No apparent external change was found but its weight showed a 8% decrease owing to biodegradation by microorganims.

EXAMPLE 12

In a twin roll, a polycondensate (product of ZENECA K.K.) between 3-hydroxybutyric acid and 3-hydroxyvaleric acid and poly-ε-caprolactone (product of Union Carbide Corp.) were charged at a ratio of 7:3 and kneaded. The aliphatic polyester so obtained was hot pressed at 160° C. for 5 minutes, whereby a sheet of 0.1 mm thick was obtained. In a similar manner to Example 8, the release rate of Z-11-tetradecenyl acetate from the sheet was measured. As a result, the sheet continued uniform release for about 40 days at a rate of 2.1 mg/day and was found to have excellent releasability.

The above sheet-shaped dispenser had a release surface area of 12 cm², and the ratio (I/II) of the aliphatic polyester was 2.9.

When the above dispenser was buried in the ground from April to October, it was worn out and almost disappeared.

EXAMPLE 13

Two tube-shaped dispensers formed in Example 9 were placed side by side. Ends at the same side of these two dispensers were heat sealed, whereby a cyclic-shaped dispenser was formed.

To a peach tree, 10 cyclic dispensers so formed were attached. Five of them were attached so that the branch of the tree is passed through a cyclic portion formed by opening the space between two tube-shaped dispensers and the remaining five dispensers were attached by winding each of the dispensers around the branch and then passing one end of the dispenser through the cyclic portion formed by the other end of the dispenser and the branch.

They were installed from April to August. No dispensers fell down and were found to be suited for practical use.

As is apparent from the above description, the biodegradable pheromone dispenser according to the second group of the present invention makes it possible to release the hormone stably, thereby conducting pest control over a long period of time. In addition, owing to biodegradability, it does not need collection after application and is therefore labor saving. Furthermore, it is degraded completely by microorganisms and does not remain in the soil so that it is excellent from the viewpoint of environmental protection.

3. Biodegradable Pest Controlling Agent (according to the third group of the invention)

No particular limitation is imposed on the biodegradable aliphatic polyester usable for the biodegradable pest controlling agent of the third group of the present invention insofar as it has biodegradability. Those exemplified above in the first group of the invention can be used. The aliphatic polyesters can be used either singly or in combination.

It is necessary that the amount of the biodegradable aliphatic polyester falls within a range of from 30 to 95 wt. % of that of the biodegradable pest controlling agent of the third group of the present invention. At amounts smaller than 30 wt. %, sufficient biodegradability cannot be secured and therefore an object of the present invention cannot be attained. Amounts larger than 95 wt. %, on the other hand, lead to a small content of the active ingredient, which makes it difficult to secure a sufficient release rate. Amounts outside the above range are therefore not suited. The amount of the aliphatic polyester preferably falls within a range of from 50 wt. % to 90 wt. %.

Any ingredient having physiological activities such as attracting activity, repellent activity and aromatic activity or pesticidal activities such as insecticidal activity can be employed without particular limitation. These active ingredients can be used either singly or in combination, for example, combination of at least two ingredients having attracting activity or combination of ingredients having attracting activity and insecticidal activity, respectively to attract and destroy insects. It is only necessary to determine the active ingredient as needed according to the object of the pest control and no limitation should not be imposed on its selection. More specifically, active ingredients exemplified above in the first group of the present invention can be used.

The content of these active ingredients is required to fall within a range of from 2 to 60 wt. %. Contents less than 2 wt. % fail to secure a sufficient release rate and are therefore not suited. Contents greater than 60 wt. %, on the other hand, are accompanied with the problems of insufficient sustained release and bleeding of the active ingredient. In order to secure more appropriate releasability, the content is desired to fall within a range of from 2 to 40 wt. %.

No particular limitation is imposed on the carrier capable of holding the active ingredient at a high content insofar as it is a polymeric material which permits the formation, by the active substance, of a solution or suspension at a temperature not lower than the melting point of the biodegradable aliphatic polyester to be used, or an inorganic or organic filler. Examples of such a polymeric material include poly-ε-caprolactone, ethylene-vinyl acetate copolymer, ethylene-ethyl acrylate copolymer, polyvinyl chloride, polyvinyl acetate, polymethacrylic esters, cellulose derivatives such as cellulose acetate butyrate, polystyrene, polyethylene, polypropylene, polybutadiene and polyisoprene. Among them, poly-ε-caprolactone, ethylene-vinyl acetate copolymer, ethylene-ethyl acrylate copolymer, polyvinyl chloride, polyvinyl acetate, polymethacrylic esters, and cellulose derivatives such as cellulose acetate butyrate can be used suitably.

No particular limitation is imposed on the filler insofar as it is an inorganic or organic filler. Examples include inorganic fillers, for example, metallic powder such as iron powder, silicic acid, silicate, alumina, calcium carbonate, barium sulfate, gypsum, slate powder, mica, kaolin, clay, talc, asbestos, graphite, carbon black and cement and organic fillers such as linter and wood meal. These fillers differ in the holding capacity of the active ingredient according to the kind, size of the particles or shape so that those having an oil absorption amount of at least 15 ml are preferably used. The larger the oil absorption amount, the larger the holding capacity of the active ingredient and the easier the mixing and dispersion work of the active ingredient. It is more preferred to use the filler having an oil absorption amount of at least 30 ml. The term "oil, absorption amount" as used herein is determined based on the testing method specified in JIS K 5105-1965 and it means the amount of an oil which can be kneaded with 100 g of a filler.

It is necessary to use the carrier such as a polymeric material or filler in an amount ranging from 2 to 50 wt. %. Amounts less than 2 wt. % are insufficient for holding the active ingredient, while amounts exceeding 50 wt. % make it impossible to control the release of the active ingredient, whereby release over a long period time cannot be secured. Amounts outside the above range are therefore not suited. More preferably, the amount falls within a range of from 5 to 40 wt. %.

The biodegradable pest controlling agent according to the present invention can be formed into a desired shape by subjecting the raw materials to the ordinarily employed molding or forming means such as heated rolls, calendering, extrusion, injection molding, blow molding, press molding or vacuum molding. No particular limitation is imposed on the shape insofar as it is suitable for pest control. Pest controlling agents of any shape can be used insofar as they fit their using purpose. Shapes of the agent will hereinafter be illustrated in FIGS. 4 to 7.

Figure 4:
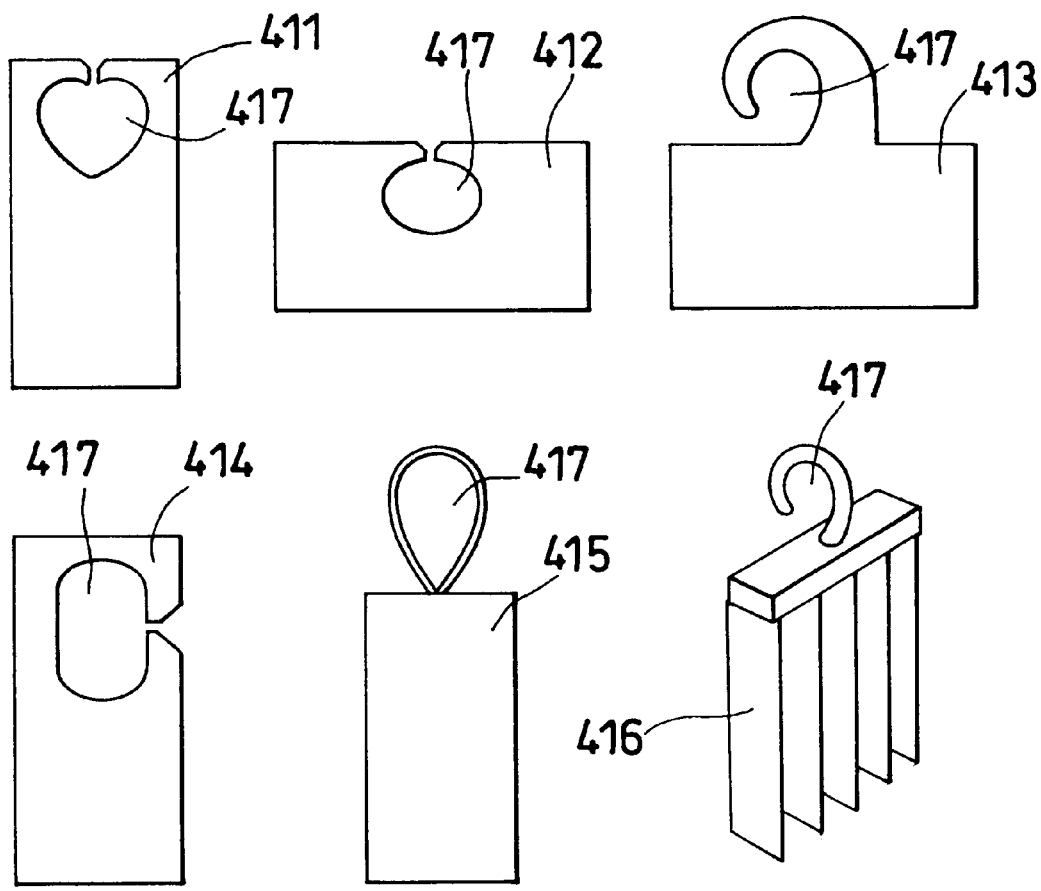
FIG. 4 is a perspective view schematically illustrating the shape of a biodegradable pest controlling agent according to the third group of the present invention.

FIG. 4 illustrates pest controlling agents 411 to 416 shaped to have a hanging hole or suspending part 417 from the material to be treated. Those of 411 to 415 are a plat type and that of 416 is a corrugated type.

Figure 5:
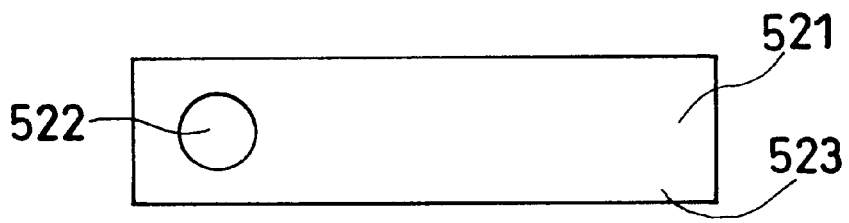
FIG. 5 is a perspective view schematically illustrating another shape of the biodegradable pest controlling agent according to the third group of the present invention.

FIG. 5 illustrates a film-shaped agent 521 having a hole 522 at one end and it is used by inserting the other end 523 to the hole.

Figure 6:
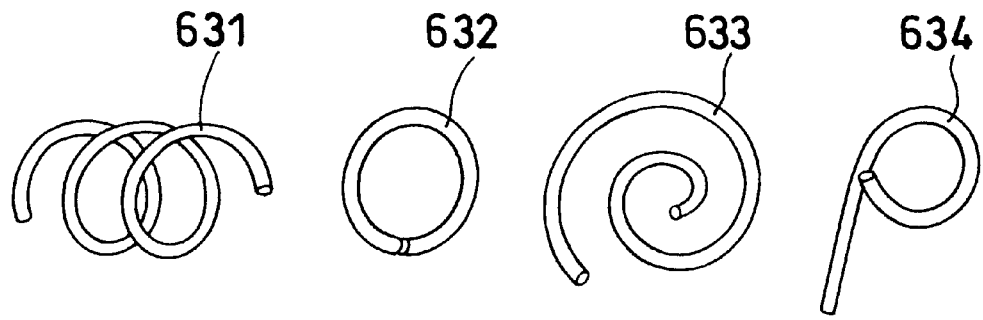
FIG. 6 is a perspective view schematically illustrating a further shape of the biodegradable pest controlling agent according to the third group of the present invention.

In FIG. 6, illustrated as 631, 632, 633 and 634 are coil-spring-, ring-, spiral- and 9-shaped agents, respectively.

Figure 7:
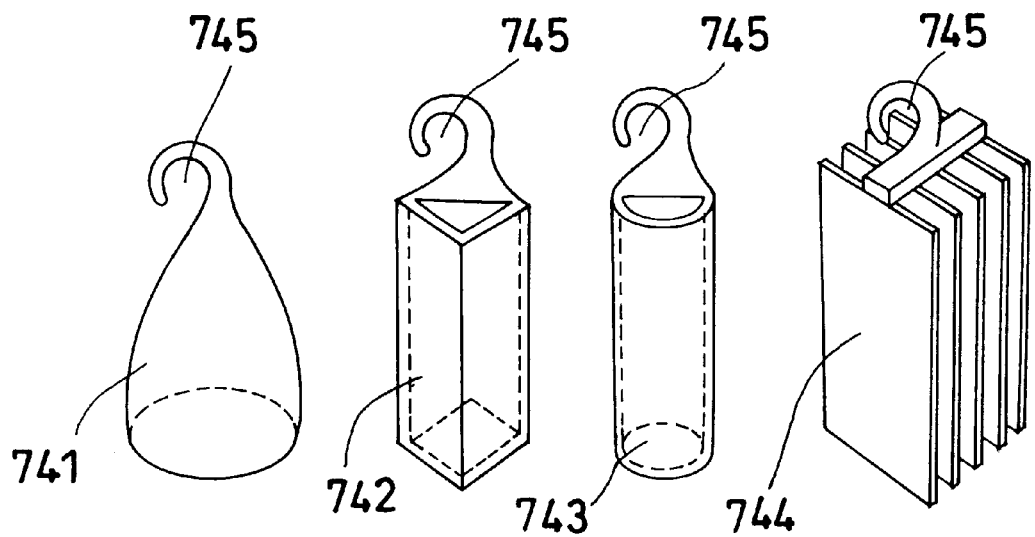
FIG. 7 is a perspective view schematically illustrating a still further shape of the biodegradable pest controlling agent according to the third group of the present invention.

In FIG. 7, illustrated as 741, 742, 743 and 744 are campanulate-, column-, pipe- and gather-shaped agents, respectively. These agents from 741 to 744 can be attached to the material to be tested by hanging the agent from the material by a hanging portion 745 or by winding the agent around the material.

In addition to the shapes as illustrated above in FIGS. 4 to 7, the biodegradable pest controlling agent according to the present invention can be used in the form of chips obtained by cutting the sheet into pieces or in the form of finely-pulverized powders. These agents can be adhered to the material to be treated by coating their surface with an adhesive and then distributing the adhesive-coated agents by aerial application or by using an applicator.

The biodegradable pest controlling agent according to the third group of the present invention needs to maintain its original performance during application so that a stabilizer such as ultraviolet absorber or antioxidant, pigment or dye may be added for the improvement of its weather resistance.

Examples of the third group of the present invention will hereinafter be given. It should however be borne in mind that the third group of the present invention will not be limited to or by the following examples.

EXAMPLE 14

50 wt. % of "Bionolle 3010" (trade name; product of Showa Highpolymer Co., Ltd.) as a biodegradable aliphatic polyester, 20 wt. % of polycaprolactone ("Tone", trade name; product of Union Carbide Corp.) as a polymeric carrier, 10 wt. % of silicic anhydride (product of Nippon Aerosil Co., Ltd.) as a filler, and 20 wt. % of Z,Z/E-7,11-hexadecadienyl acetate, which was a sex pheromone of *Pectinophora gossypiella*, as an active ingredient were mixed, followed by kneading in a triple roll. The kneaded mass was rolled into a sheet of 0.5 mm thick.

The sheet so obtained was cut into strips of 20 mm in width and 50 mm of length, whereby a pest controlling agent was prepared. The agent so obtained was left alone under the conditions at 40° C. and 0.5 m/s and the release rate therefrom was measured. As a result, it showed a release rate of at least 1.8 mg/day over about 45 days and showed excellent results.

Incidentally, the controlling agent was buried in the ground from April to October and then it partially disappeared. Even the remaining portion was torn out and progress of biodegradation was observed.

To 2 g of Z,Z/E-7,11-hexadecadienyl acetate was added 0.5 g of the above polycaprolactone and they were stirred under heat to 96° C., the melting point of "Bionolle 3010", whereby a transparent viscous liquid was obtained. The oil absorption amount of silicic anhydride was 148 ml.

EXAMPLE 15

In a similar manner to Example 14, a sheet of 0.5 mm in thickness was formed. The sheet so obtained was cut into strips of 40 mm in width and 50 mm in length, whereby a pest controlling agent was prepared. The agent so obtained was left alone under the conditions at 40° C. and 0.5 m/s and the release rate was measured. The agent showed a release rate of at least 3.5 mg/day over about 40 days. The release rate was adjusted easily by changing the release area.

Incidentally, when the above controlling agent was buried in the ground from April to October, biodegradation of it proceeded to the same degree as in Example 1.

EXAMPLE 16

In a similar manner to Example 14 except that the kneaded mass was rolled into a sheet of 0.25 mm thick, a pest controlling agent in the form of strips was prepared. The release rate of the agent so obtained was measured under the conditions at 40° C. and 0.5 m/s. As a result, it showed a release rate of at least 1.8 mg/day over about 20 days. By changing the thickness, the release period was regulated easily.

Incidentally, when the above controlling agent was buried in the ground from April to October, biodegradation of it proceeded and it almost disappeared.

COMPARATIVE EXAMPLE 13

In a similar manner to Example 14, 80 wt. % of "Bionolle" (trade name; product of Showa Highpolymer Co., Ltd.)

and 20 wt. % of Z,Z/E-7,11-hexadecadienyl acetate were kneaded in a triple roll. As a result, the absorption of Z,Z/E-7,11-hexadecadienyl acetate was poor and it sagged down from the roll. Thus, it was inferior in processing property.

To 2 g of Z,Z/E-7,11-hexadecadienyl acetate was added 0.5 g of "Bionolle 3010", followed by stirring under heat at 96° C. As a result, Z,Z/E-7,11-hexadecadienyl acetate and "Bionolle 3010" were separated into two phases and neither solution nor suspension was formed.

COMPARATIVE EXAMPLE 14

In a similar manner to Comparative Example 13, 8 g of "Bionolle 3010" (trade name; product of Showa Highpolymer Co., Ltd.) and 2 g of Z,Z/E-7,11-hexadecadienyl acetate were mixed, to which 50 ml of methylene chloride were added to form a solution. The resulting solution was cast on a glass plate, whereby a film-shaped controlling agent having a thickness of 0.12 mm was obtained.

On the surface of the controlling agent so obtained, Z,Z/E-7,11-hexadecadienyl acetate, that is, the active ingredient, bled and stuck to hands. Thus, the film-shaped agent was not appropriate. Furthermore, the film had no rigidity and was therefore inferior in hanging property.

EXAMPLE 17

Mixed were 40 wt. % of "Bionolle 1010" (trade name: product of Showa Highpolymer Co., Ltd.) as a biodegradable aliphatic polyester, 25 wt. % of polyvinyl acetate (product of Aldrich Chemical Co., Inc.) as a polymeric carrier, 15 wt. % of calcium carbonate (product of Nitto Funka Kogyo K.K.) as a filler and 20 wt. % of Z-11-tetradecenyl acetate, which was a sex pheromone of a leaf folder, as an active ingredient, followed by kneading in a triple roll. The resulting mass was rolled into a sheet of 0.5 mm thick.

The sheet so obtained was cut into strips of 30 mm wide and 70 mm long. At the upper part of each of the strips, a hanging hole having a diameter of 1 cm was made, whereby a pest controlling agent was prepared. In an apple farm of 30 a, 180 strips were placed and from the middle of May to the middle of August, an attraction and inhibition rate of *Adoxophyes orana* Fischer von Rö}slerstamm was measured. The agent showed effects as high as 99.0%.

When the pest controlling agent so obtained was buried in the ground from April to October, it partially disappeared and even the remaining portion was degraded so that it was torn out easily.

To 2 g of Z-11-tetradecenyl acetate was added 0.5 g of the above polyvinyl acetate and they were stirred under heat to 114° C., the melting point of "Bionolle 1010", whereby a transparent viscous liquid was obtained.

The oil absorption amount of calcium carbonate was 36 ml.

EXAMPLE 18

In a twin roll, a mixture of 90 wt. % of "Biopole" (trade name; product of ZENECA K.K.) as a biodegradable aliphatic polyester, 2 wt. % of an ethylene-vinyl acetate copolymer (product of Sumitomo Chemical Co., Ltd.), which had a vinyl acetate content of 41%, as a polymeric carrier, 2 wt. % of talc (product of Nippon Talc Co., Ltd.) as a filler type carrier and 6% of Z-8-dodecenyl acetate, which was a sex pheromone of *Grapholita molesta*, as an active ingredient was kneaded, followed by pulverization in a pulverizer, whereby powders of 42 mesh were obtained.

To 400 g of the powders so obtained, 15 kg of an adhesive ("Vinibran 2580", trade name; product of Nisshin Chemical Industry Co., Ltd.) were added, followed by dispersing in water. The resulting dispersion was applied to a peach garden of 20 a in the middle of April by an applicator. From the middle of April to the end of May, an attraction and inhibition rate of *Grapholita molesta* was measured. The agent showed an inhibition rate of 100% and the results are therefore satisfactory.

In one place of the ground, 1 g of the pest controlling agent in the powdery form was buried and was left alone from April to October. As a result of digging up, a white trace remained, but powdery granules disappeared completely and were not confirmed.

To 2 g of Z-8-dodecenyl acetate was added 0.5 g of the above ethylene-vinyl acetate copolymer and they were stirred under heat to 144° C., the melting point of "Biopole", whereby a transparent viscous liquid was obtained. The oil absorption amount of talc was 31 ml.

COMPARATIVE EXAMPLE 15

In a similar manner to Example 18 except that 96 wt. % of "Biopole" (product of ZENECA K.K.), 2 wt. % of an ethylene-vinyl acetate copolymer (product of Sumitomo Chemical Co., Ltd.), as a polymeric carrier, having a vinyl acetate content of 41% and 2% of Z-8-dodecenyl acetate, which was a sex pheromone of *Grapholita molesta*, as the active ingredient, powders of 42 mesh were prepared.

To 1200 g of the powders so obtained, 20 kg of an adhesive ("Vinibran 2580", trade name; product of Nisshin Chemical Industry Co., Ltd.) were added, followed by dispersing in 200 l of water. The resulting dispersion was applied to a peach garden of 20 a in the middle of April by an applicator. As a result of measurement of an attraction and inhibition rate of *Grapholita molesta* from the middle of April to the middle of May, it was 76.2% and was therefore insufficient. Amount of the powders consumed was 1200 g, which showed that this agent was not economical.

EXAMPLE 19

Mixed were 30 wt. % of polycaprolactone (product of Union arbide Inc.; 30 wt. %), 10 wt. % of an ethylene-vinyl acetate copolymer (product of Sumitomo Chemical Co., Ltd.), which had a vinyl acetate content of 41%, as a polymeric carrier, 10 wt. % of silicic anhydride (product of Nippon Aerosil Co., Ltd.) as a filler and 50 wt. % of Z-11-tetradecenyl acetate as an active ingredient, followed by the formation into a tubular pest controlling agent having an internal diameter of 8 mm, an outer diameter of 10 mm and length of 40 mm by an extruder. The tubular pest controlling agent so obtained was placed in an apple garden at a ratio of 60 pieces/20 a by putting each agent through a branch. An attraction and inhibition ratio of *Adoxophyes orana* Fischer von Rö}slerstamm was measured from the middle of May to the middle of August. As a result, the rate was as high as 99.5%, which showed that the agent was highly effective.

When the tubular pest controlling agent was buried in the ground from April to October, it lost its original shape and was worn out.

To 2 g of Z-11-tetradecenyl acetate was added 0.5 g of, as a polymeric carrier, an ethylene-vinyl acetate copolymer (product of Sumitomo Chemical Co., Ltd.) having a vinyl acetate content of 41% and they were stirred under heat to 60° C., the melting point of polycaprolactone, whereby a transparent viscous liquid was obtained. The oil absorption amount of silicic anhydride was 148 ml.

COMPARATIVE EXAMPLE 16

In a similar manner to Example 19 except that 20 wt. % of polycaprolactone, 10 wt. % of, as a polymeric carrier, an ethylene-vinyl acetate copolymer having a vinyl acetate content of 41%, 5 wt. % of silicic anhydride as a filler and 65 wt. % of Z-11-tetradecenyl acetate as an active ingredient were mixed, a tubular pest controlling agent having an internal diameter of 8 mm, an outer diameter of 10 mm and length of 40 mm was formed. On the surface of the tubular pest controlling agent so obtained, Z-11-tetradecenyl acetate bled and became sticky. The agent was inconvenient for handling and besides, it was accompanied with the drawback that the tube was crushed easily when it was put through a branch of an apple tree. Thus, it was not suited for practical use.

EXAMPLE 20

A mixture composed of 60 wt. % of "Bionolle 1010" (trade name: product of Showa Highpolymer Co., Ltd.) as a biodegradable aliphatic polyester, 20 wt. % of, as a polymeric carrier, an ethylene-ethyl acrylate copolymer (product of Nippon Unicar Co., Ltd.) having an ethyl acrylate content of 10% and 20 wt. % of, as an active ingredient, E,E-8,10-dodecadienol, a sex pheromone of codlin moth (*Cydia pomonella*), was kneaded in a roll. The resulting mass was rolled into a sheet of 0.5 mm thick. From the sheet so obtained, a strip of 20 mm wide and 50 mm long was cut out. The release rate from the strip was measured under the conditions at 30° C. and 1 m/s. As a result, it continued release for about 50 days at a rate of at least 1.5 mg/day and was found to be suited for long-time release.

When the strip-shaped pest controlling agent so obtained was buried in the ground from April to October, it partially disappeared and even the remaining portion was degraded so that it was torn out easily by hands.

The above ethylene-ethyl acrylate copolymer having an ethyl acrylate content of 10% was stirred under heat to 114° C., the melting point of "Bionolle 1010", whereby a turbid viscous suspension was obtained.

COMPARATIVE EXAMPLE 17

In a similar manner to Example 20 except that 25 wt. % of "Bionolle 1010", 55 wt. % of an ethylene-ethyl acrylate copolymer and 20 wt. % of E,E-8,10-dodecadienol were used, a strip-shaped pest controlling agent was prepared. As in Example 20, the release rate of the agent so obtained was measured under the conditions at 30° C. and 1 m/s. As a result, the release from the agent was excessive at the beginning but after that, showed a gradual decrease drastically. Thus it was not suited for practical use. Incidentally, the release at the rate of 1.5 mg or larger was secured for 27 days.

Similarly to Example 20, the pest controlling agent was buried in the ground from April to October. As a result, no change was observed except the slight discoloration on the surface and degradation had not proceeded.

As is apparent from the above description, it has been found that the use of a biodegradable pest controlling agent according to the third group of the present invention makes it possible to control pests over a long period of time; and owing to biodegradability, does not need collection after application and is therefore labor saving. In addition, the agent is degraded by microorganisms and loses its original shape so it is excellent from the viewpoint of environmental protection. Moreover, the biodegradable pest controlling agent according to the present invention can be prepared easily so that it is economically excellent. It is also possible to easily carry out regulation of the release rate or useful life or processing into a desired shape, whereby the number of the agents applied can be reduced. The agent is also suited for aerial application when formed into powders.

The entire disclosure of Japanese Patent Applications Nos. 8-168898, 8-168899 and 8-168900 filed on Jun. 28, 1996 including specifications, claims, drawings and summaries are incorporated herein by reference in its entirety.

We claim:

1. A biodegradable sustained-release preparation which comprises a mixture of 99 to 10 parts by weight of an aliphatic polyester and 1 to 90 parts by weight of a modifier for the regulation of sustained releasability of an active ingredient; and the active ingredient held by said mixture.

2. A preparation according to claim 1, wherein an equilibrium swelling ratio at 40° C. of the modifier to the active ingredient was at least 2 wt. %.

3. A preparation according to claim 1, wherein the active ingredient is a pheromone.

4. A preparation according to claim 1, wherein the modifier is at least one compound or mixture of at least two compounds selected from the group consisting of poly-ε-caprolactone, polyvinyl acetate, ethylene-vinyl acetate copolymer, ethylene-ethyl acrylate copolymer, polyvinyl chloride, polymethacrylic esters and cellulose derivatives.

5. A biodegradable sustained-release preparation, wherein the active ingredient is encapsulated in a container formed of the mixture as claimed in claim 1 and the mixture controls the release of the active ingredient.

6. A preparation according to claim 2, wherein the active ingredient is a pheromone.

7. A preparation according to claim 2, wherein the modifier is at least one compound or mixture of at least two compounds selected from the group consisting of poly-ε-caprolactone, polyvinyl acetate, ethylene-vinyl acetate copolymer, ethylene-ethyl acrylate copolymer, polyvinyl chloride, polymethacrylic esters and cellulose derivatives.

8. A preparation according to claim 3, wherein the modifier is at least one compound or mixture of at least two compounds selected from the group consisting of poly-ε-caprolactone, polyvinyl acetate, ethylene-vinyl acetate copolymer, ethylene-ethyl acrylate copolymer, polyvinyl chloride, polymethacrylic esters and cellulose derivatives.

9. A preparation according to claim 6, wherein the modifier is at least one compound or mixture of at least two compounds selected from the group consisting of poly-ε-caprolactone, polyvinyl acetate, ethylene-vinyl acetate copolymer, ethylene-ethyl acrylate copolymer, polyvinyl chloride, polymethacrylic esters and cellulose derivatives.

* * * * *